United States Patent [19]

Spewock et al.

[11] 4,069,714
[45] Jan. 24, 1978

[54] METHOD FOR MEASURING PHYSICAL DATA BY MAGNETIC MEANS

[75] Inventors: Sandra Spewock, Franklin Township, Cambria County; David C. Phillips, Penn Hills Township, Allegheny County, both of Pa.

[73] Assignee: Westinghouse Electric Corporation, Pittsburgh, Pa.

[21] Appl. No.: 655,350

[22] Filed: Feb. 5, 1976

[51] Int. Cl.² .................. G01K 7/38; G01N 31/12; G01R 33/16
[52] U.S. Cl. ................... 73/339 R; 73/27 A; 73/362 CP; 23/253 TP; 324/224; 324/204; 324/202
[58] Field of Search .............. 73/27 A, 86, 362 CP, 73/339 R; 23/253 TP; 324/345, 34 TA; 340/228 F

[56] References Cited

U.S. PATENT DOCUMENTS

| | | | |
|---|---|---|---|
| 2,756,595 | 7/1956 | Rathenau et al. | 73/339 R |
| 3,299,348 | 1/1967 | Beauxis, Jr. et al. | 324/345 |
| 3,714,564 | 1/1973 | Reinnagel | 324/34 R X |
| 3,839,898 | 10/1974 | Talboom, Jr. et al. | 73/339 R X |
| 3,918,910 | 11/1975 | Soya et al. | 23/253 TP X |
| 3,965,724 | 6/1976 | Ambrose | 73/339 R X |

OTHER PUBLICATIONS

Rayl, et al.; "Magnetic Gas Sensor"; Conference on Magnetic Materials; Philadelphia, Dec. 1975.

*Primary Examiner*—Richard C. Queisser
*Assistant Examiner*—John S. Appleman
*Attorney, Agent, or Firm*—C. M. Lorin

[57] ABSTRACT

A strip of material is reacted in situ with a chemical agent so as to create a chemical change affecting the magnetic properties of the material. From past history with the same kind of strip under identical conditions of reactions with the chemical agent, data such as time of exposure, temperature and partial pressure are recorded providing a calibration of any sensed magnetic property changes in such strip. An accurate direct measurement is thus made possible with an identical strip exposed to unknown temperature or partial pressure, by sensing of the degree of magnetization of the strip.

4 Claims, 5 Drawing Figures

METHOD FOR MEASURING PHYSICAL DATA BY MAGNETIC MEANS

CROSS REFERENCE TO RELATED PENDING PATENT APPLICATIONS

The present application is related to the following concurrently filed patent application which is assigned to the same assignee as the present application: Ser. No. 655,349 which was filed on Feb. 5, 1976 by W. M. Hickam.

BACKGROUND OF THE INVENTION

The invention relates to a novel and unique memory device for directly and continuously storing information relative to partial pressure, or temperature, in an industrial process.

The invention relates more particularly to memory devices including, as storing element, material possessing magnetic domains.

Memory devices are classified as non-destructive and as destructive. Non-destructive memory devices afford the possibility to write and read then erase and again write information data. The destructive type can permit repetitive reading, but the information is permanently stored in the storing medium. A read only memory is typical of this second type.

Magnetic memory devices generally take advantage of the fixed orientation taken by magnetic moments under the effect of an external magnetic field, thus creating a magnetic condition in the material which can be read at a later time. In that sense, a magnetic memory device, in the prior art, is always non-destructive since a change of orientation of magnetic moments does not affect the fundamental structure of the material.

Read-only memory devices, nevertheless, have been manufactured in the past with such non-destructive memories by combining memory elements and by so separating electrically the zones of exposure to external influence that changes effected in one zone become irreversible in relation to another zone.

A common type of magnetic memory device is the magnetic tape used in sound recording or as an integral part of a computer. The magnetic tape in sound recording is not exposed directly to the effects of the acoustic waves. A transducer device is necessary in order to convert the acoustic wave into an electrical signal used to impress on the tape a corresponding magnetic field altering the magnetic state of the tape. With the electronic computer, data information is stored into the tape at the input side by electromechanical means, which also are in substance a transducer.

Attempts have been made already to apply the magnetic storing quality of magnetic materials to recording and monitoring of physical phenomena, and more particularly as a means for on-line chemical analysis of chemical reactions. For instance, in the U.S. Pat. No. 3,868,059 issued 2-25-75 to W. M. Hickam et al, assigned to the same assignee as the assignee of the present application, and entitled "Magnetic Bridge-Type Meter For Magnetically Permeable Particulate Matter", is described apparatus for the detection of fly ash emitted in the exhaust of a coal-fired furnace. The fly ash is admitted into the air gap of a permanent magnet associated with a magnetic bridge circuit and the change in inductance, thus caused, is detected as an indication of the operative conditions of the furnace. Therefore, the Hickam patent shows an apparatus having inherent magnetic characteristics which is directly exposed to an external physical phenomenon to be sensed and monitored, with the altered magnetic characteristics being used for detection and monitoring of the external physical phenomenon.

In the same vein, it is known from a paper presented at a Conference on Magnetic Materials held at Philadelphia in December 1975, entitled "Magnetic Gas Sensor" by Martin Rayl, Peter J. Woytowicz and Harold D. Hanson, to expose the core of an electromagnetic coil to oxidation-reduction reaction by gases, so that chemical changes occur in the material and the resulting change in inductance is measured as an indication of the presence of the gas.

Still, the prior art does not fulfill all the major needs of the industry regarding the acquisition of data relative to physical parameters in situ.

The present invention stems from the teachings set forth in the afore-mentioned copending Hickam patent application and proposes to expose a magnetic tape to a physical, or chemical agent, thereby to store into the material of the tape chemical changes which permanently affect the magnetic properties of the tape, and to sense such altered magnetic properties as an indication of the physical, or chemical, agent presence involved in such changes, as well as of process physical parameters involving such physical, or chemical, agent.

The present invention is a novel approach to measuring temperature, or partial pressure, and storing information regarding such measured temperature or partial pressure as a function of time with respect to materials, industrial and chemical processing of materials, and/or physical phenomena.

One object of the present invention is to measure temperature, or partial pressure, in situ by storing chemical changes due to temperature in a selected material.

Another object of the invention is to store chemical changes, due to temperature, or partial pressure changes, into material exposed in situ to such changes as a function of time.

A further object of the invention is to provide material susceptible of permanent chemical changes which are indicative of a predetermined temperature level, or partial pressure level, reached under exposure.

Still another object of the invention is to measure temperature, or partial pressure, by sensing the magnetic properties of material exposed to temperature.

The present invention relates to a novel approach to measuring temperature, or partial pressure and storing such information as a function of time, in situ in the high temperature range, mainly from 500° to 1600° C.

The measurement of temperature is important for many industrial applications. Temperature reveals the progress of a thermal treatment and indicates physical as well as chemical changes imparted by heat or chemical reaction to a processed material, especially in the case of metal processing. Temperature is also an essential parameter indicative of the operative condition of a furnace.

The thermometer and the dilatometer are not applicable in a temperature range in excess of 200° C. For very high temperatures, for instance the temperature of a furnace, temperatures have been measured by optical means responding to the spectrum of a light radiation emitting body. However, these are laboratory instruments which are costly, which require expertise in handling. Another drawback stems from the fact that the information gathered must be interpreted and is not directly storable. These instruments also are suitable only for extremely high temperatures and could not be used for measuring temperature of a black body.

There is a need for combining the precision of a scintillometer with the easy handling afforded by the conventional thermometer. In this regard, the invention can be used in situ within the confines of a high temperature furnace, gas, fluid or solid.

The present invention makes use of the property of certain chemical materials when exposed to a chemical agent having affinity therewith, to react in increasing proportion as a function of time of exposure, of the amount of chemical agent and/or of temperature. By a proper selection of the size and weight of the basic chemical material, knowing the precise conditions of exposure and duration thereof, the product of chemical reaction can be ascertained, and conversely, knowing the reaction product and all the parameters of the reaction except one, the latter can be known exactly by magnetic sensing.

The invention proposes to select solid material having stable physical and chemical characteristics at ambient temperature which, thus, can be used for storage of information, a quality which, for instance, conventional thermometers do not have.

The preferred physical parameter selected for characterizing the ultimate stage of the chemical reaction reached in the material is the magnetic properties, whereby by sensing a magnetic field, or measuring an inductance, an indication of the temperature having permanently modified the critical chemical composition of the material, e.g., of the maximum or minimum temperature experienced by the material, can be detected.

SUMMARY OF THE INVENTION

The present invention resides in a magnetic tape, or strip, for on-line sensing and storing of the temperature, or the partial pressure, of gases, liquids and solids, in an industrial process.

The magnetic tapes according to the present invention may be used for sampling, sensing, recording, controlling, and data storage of physical and chemical properties of gases, liquids, and solids. Magnetic, or non-magnetic, materials are placed on a flexible non-interfering substrate and passed, at a predetermined speed rate, through the physical or chemical environment in which temperature, or the partial pressure is to be measured, monitored or controlled.

Alteration, in any or all magnetic properties of the materials, induced as a result of chemical changes due to a chemical agent and to temperature can be later read out by magnetic sensors. The noted changes in magnetic response are interpreted in terms of their relationship to definite temperature levels, or partial pressure levels, of the chemical agent reached by the environment, to which the materials were exposed, or variations thereof from specified or reference environment conditions.

DESCRIPTION OF THE PREFERRED EMBODIMENT

Figure 1:
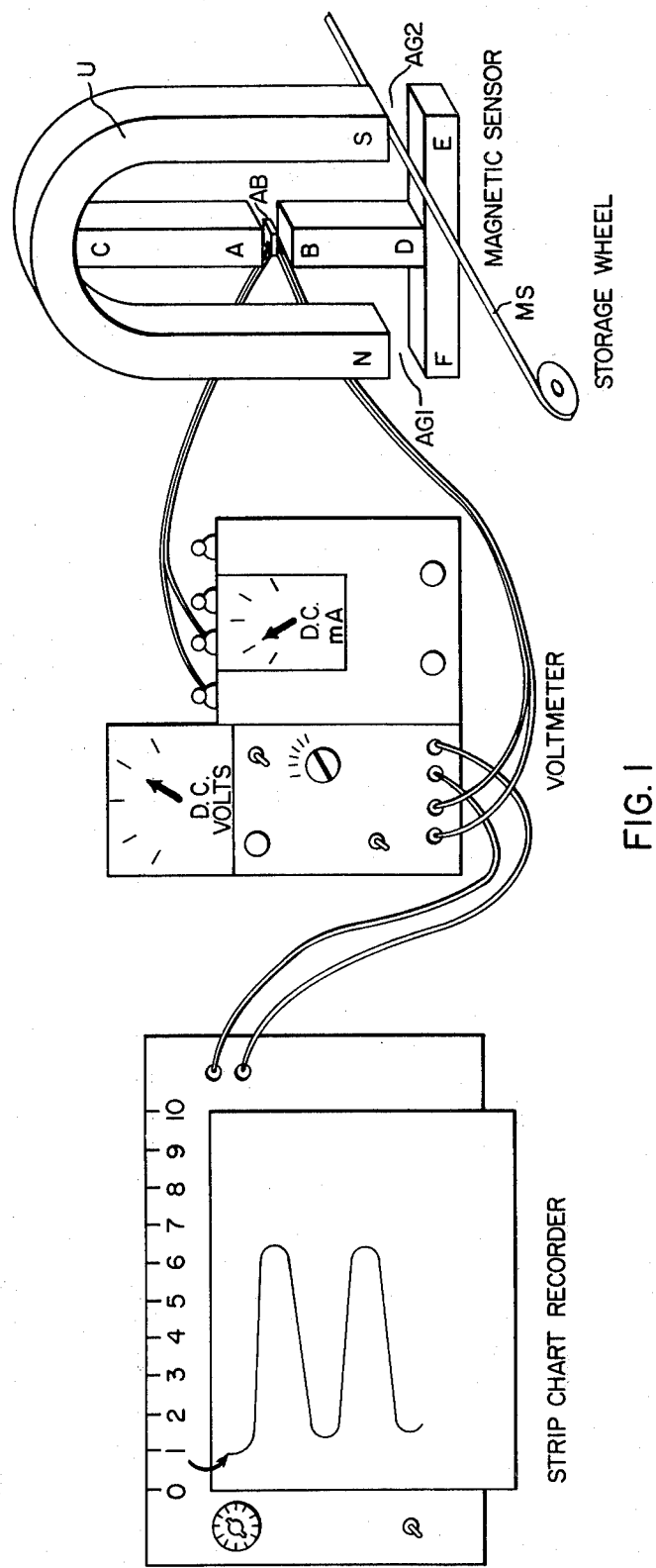
FIG. 1 shows apparatus for sensing magnetic tape used in accordance with the present invention.

The invention resides in a magnetic tape, or strip, for on-line sensing and storing of the temperature or partial pressure, of a chemical element evolving from gases, liquids or solids, and in the industrial application of such stored information for monitoring, sampling, recording, process control and data storage.

By "magnetic tape" in the description given hereafter is to be understood any magnetic or non-magnetic recording medium of sufficient length, of a given width or even as a wire, homogeneous or coated, made of magnetic or non-magnetic material in continuous form or discretely applied or deposited, which has been selected in accordance with the teachings of the present invention, as explained hereinafter.

As explained in the afore-mentioned Hickam patent application, various physical and chemical agents in the environment can alter the material in such a way that magnetic properties will be produced (if the material is initially non-magnetic) or increased or diminished (if the material is initially magnetic).

Most desired materials that can be used as a tape or strip for sensing a chemical or physical characteristic of the environment are iron, nickel, cobalt and compounds and alloys of these elements. Chemical reaction products leading to changes in the magnetic properties of the basic material may include the formation of reduction products of oxides, carbides, nitrides, hydrides, chlorides and sulfides of iron, nickel, cobalt and other elements which undergo changes in magnetic properties as a result of chemical reaction involving the material of the tape. The structural changes in the material under specific chemical agents are listed in Table 1 herebelow. Physical agents may also affect the magnetic properties of a tape. These are listed in Table 2.

TABLE 1

Chemical Agents Which Increase or Decrease the Magnetic Properties of Certain Materials

|  | Initial Reactant | Chemical Agent | Final Product |  |
|---|---|---|---|---|
|  | Ni | $H_2SO_4$ | $NiSO_4$ |  |
|  | Ni | $SO_2$ | $NiSO_4$ |  |
|  | Ni | $O_2$ | $NiO$ |  |
|  | Ni | $HNO_3$ | $Ni(NO_3)_2$ |  |
|  | Fe | $CO_2$ | $FeO$ |  |
| Magnetic | Fe | $HCl$ | $FeCl_2$ | Non-Magnetic |
| Materials | Fe | $HF$ | $FeF_2$ | Materials |

TABLE 1-continued

Chemical Agents Which Increase or Decrease the Magnetic Properties of Certain Materials

|  | Initial Reactant | Chemical Agent | Final Product |  |
|---|---|---|---|---|
|  | Fe | $HNO_3$ | $Fe_2O_3$ |  |
|  | Fe | $O_2 + H_2O$ | FeO |  |
|  | Fe | $H_2O_2$ | FeO |  |
|  | Fe | $O_3$ | $Fe_2O_3$ |  |
|  | Fe | $NO_2 + H_2$ | FeO |  |
|  | Cr | As | CrAs |  |
| Non-Magnetic | $Cr(OH)_3$ | $O_2$ | $CrO_2$ | Magnetic |
| Materials | $Fe_2O_3$ | $H_2$ | Fe | Materials |
|  | $Fe_2O_3$ | $SO_2$ | $Fe_3O_4$ |  |

TABLE 2

Physical Agents Which Increase or Decrease the Magnetic Properties of Certain Materials

|  | Initial Reactant | Physical Agent | Final Product |  |
|---|---|---|---|---|
| Non-Magnetic | $Cr(NO_3)_3$ | Heat | $CrO_2$ | Magnetic |
| Materials | 304 Stainless Steel | Cold working | 304 stainless steel (magnetic) | Materials |
|  | Ni | Heat to Curie point (360° C) | Ni |  |
|  | Fe | Heat to Curie point (768° C) | Fe |  |
| Magnetic | Co | Heat to Curie point (1120° C) | Co | Non-Magnetic |
| Materials | Ni | Any physical agent that diminishes the amount of | Ni | Materials |
|  | Fe | material present; e.g., abrasion, solvent | Fe |  |
|  | Co | dissolution, etc. | Co |  |

From Table 1 it appears that through the influence of an external chemical agent ($H_2SO_4$, $SO_2$, $O_2$, $CO_2$, . . .) applied under a given partial pressure and temperature, the magnetic tape is modified chemically by the formation in ascertainable amounts of a chemical compound ($NiSO_4$, FeO, $CrA_s$. . .) to an extent depending upon the temperature, partial pressure and time of exposure. As a result the magnetic tape exhibits after a certain time of exposure a final physical state characterized by definite new magnetic properties. For a given thickness of the original base magnetic state, the final product becomes a definite amount which forms part of the tape in its final stage. A correlation necessarily exists between the chemical agent altering of the material and the resulting magnetic change. Such correlation can be determined once for all with a magnetic tape of definite quality and thickness after exposure to the chemical agent under precisely known conditions of temperature, partial pressure and time of exposure. Thus, for a given time of exposure and a predetermined partial pressure of the chemical agent the physical change sensed magnetically on the identical type of magnetic sensor will provide a definite information regarding temperature. Conversely, with a predetermined temperature held during exposure, a definite information regarding pressure will be provided by sensing the end magnetic properties.

The induced magnetic changes of these tapes may be continuous or discrete along the tape. The alteration may affect the entire volume of the tape, or only its coating and at variable depths. The exposed layer may be in the form of a thin film, exhibiting magnetic changes as a function of the depth of the coating in response to time of exposure and/or change in the concentration of selective reactants. The coating itself may be discontinuous.

Such magnetic tapes can be used in accordance with the present invention for sampling, sensing, recording, and controlling environments in response to the permanent alterations sensed as changes in the magnetic properties of the tapes.

The magnetic tapes to be used for determining or controlling the physical and chemical properties of an environment may take several forms. Included among the possible configurations of the disclosed tapes are solid wires, solid ribbons, continuous and discontinuous coated wires and/or ribbons.

A specially designed magnetic tape is passed directly through the environment for which temperature, or partial pressure, is sought.

Once the change has been induced in the magnetic structure of the tape material, it can be read by a conventional inductance or magnetic field measuring instrument. As a result, temperature or pressure is in fact measured. However, as illustrated in FIG. 1, a special equipment has been conceived to perform such measurements. Perturbations in the field generated by a permanent magnet U are sened by a Hall effect element at AB.

The magnetic sensor comprises a horseshoe-shaped magnet U separated by two equal air gaps $AG_1$, $AG_2$ from a soft iron bar (FE). Two additional soft iron bars (CA and BD) connect the top center of the horseshoe magnet U with the center of the soft iron bar FE. Cemented between CA and BD is a small Hall effect element AB. The Hall element has two leads which carry a constant direct current input, and two leads which carry a continuous electrical output signal. The magnitude of the electrical output (or Hall voltage) is determined by the strength of the net magnetic field which the Hall element senses, as well as the size of the direct current input. When the current is constant, the net magnetic field is determined by 1) the strength of the magnet, 2) the nature of the magnetic material, and 3) the amount of magnetic material. The resulting electrical signal can be read from a voltmeter, or it can be fed to a recorder. Perturbations are caused by the presence of the tape of magnetic material in proximity to the sensor portion of the apparatus, e.g., in one of the air gaps $AG_1$, or $AG_2$. The magnitude of the signal produced depends upon the nature and amount of magnetic material. The instrument of FIG. 1 is designed to operate over a wide range of sensitivities, and capable of detecting very small perturbations. Small changes in the magnetic properties of a material can therefore be detected.

Table 3 herebelow lists the characteristics of some ferromagnetic materials. For a given magnet strength, the higher the material permeability, the larger will be the net magnetic field sensed by the Hall element, everything else remaining constant. Also, the greater the amount of magnetic material, the larger the field sensed.

TABLE 3

Some Properties of High-Permeability Materials

| Name (Composition) | m.p. (° C) | Curie Pt. (° C) | Max. Permeability | Coercive Force (oersteds) | Saturation Induction (gausses) | Saturation Hysteresis (ergs/cm$^3$) |
| --- | --- | --- | --- | --- | --- | --- |
| Iron (.2 impurity) | 1537 | 768 | 5000 | 1.0 | 21,500 | 5000 |
| Cobalt (99 Co) | 1495 | 1120 | 250 | 10 | 17,900 | 2000 |
| Nickel (99 Ni) | 1455 | 360 | 600 | 0.7 | 6,100 | 2000 |

If the device is symmetrical and the material present in the air gaps is the same, no magnetic field will be detected by the Hall element and no Hall voltage will be registered. Both the north and the south poles of the magnet "attempt" to induce a pole of opposite polarity in the soft iron bar at A. If the geometry is perfect, the two induced poles exactly cancel. Under the same symmetrical conditions, the poles induced at B cancel as well.

If a magnetic material is introduced into one of the two gaps, but not into the other, the effective permeability of the gaps is changed and the two induced poles at B no longer exactly cancel. The resulting net field produces an electrical signal — the Hall voltage — as described above. This signal can be read from a meter or it can be fed to a recorder. In addition, both the Hall voltage signal and the recorder output can be amplified so as to accommodate a wide range of materials and conditions.

Figure 2:
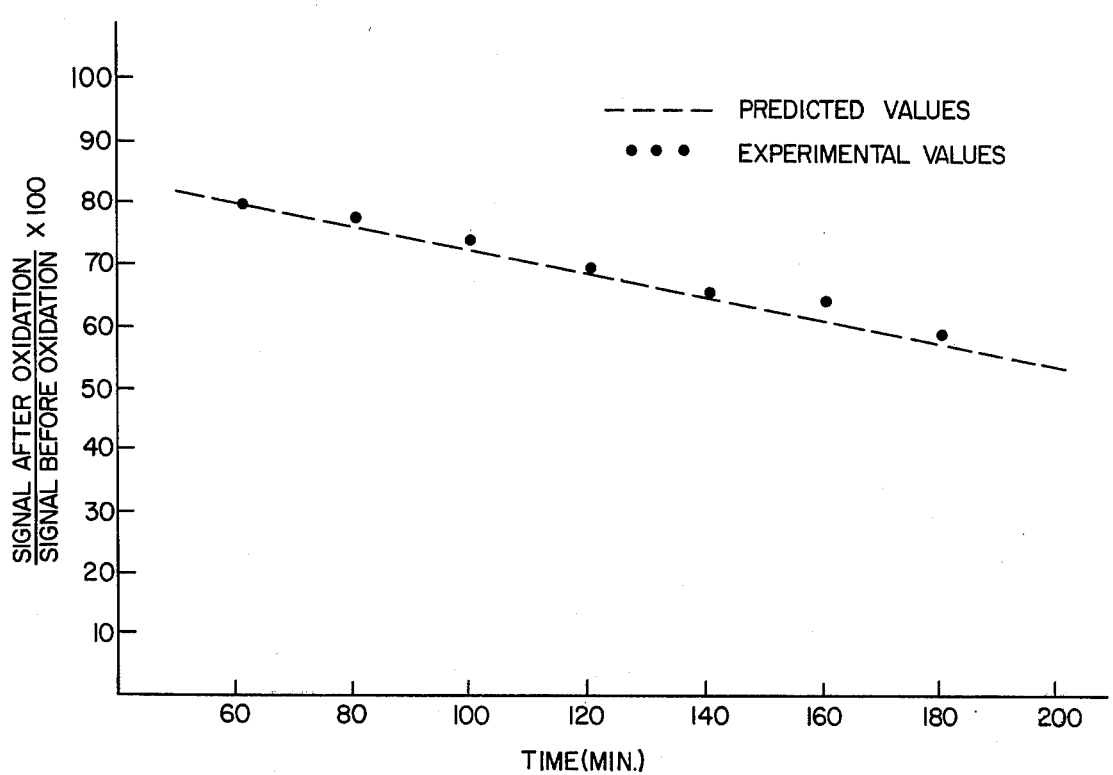
FIG. 2 is an experimental curve indicating the signal reduction due to the formation of nickel oxide for different times of exposure when sensed on an oxidized nickel foil with the apparatus of FIG. 1.
Figure 3:
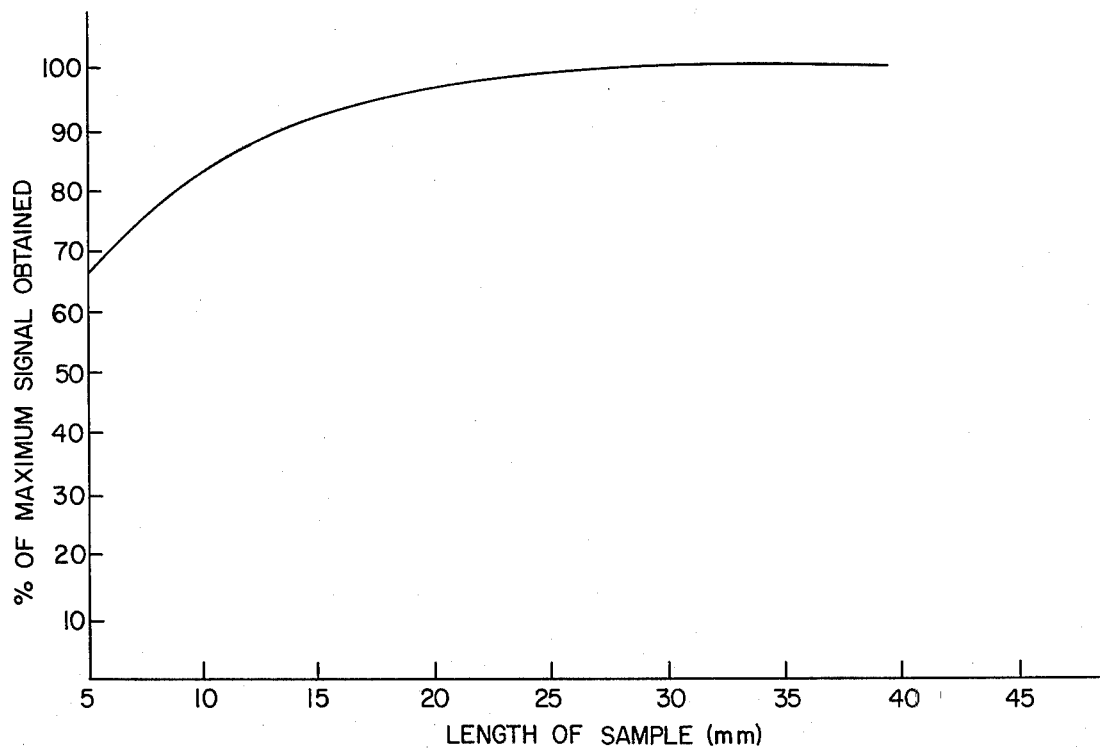
FIG. 3 shows variations in the magnitude of the signal detected by the apparatus of FIG. 1 as a function of the distance along the magnetic tape according to the invention, taken from the center of the air gap in which the magnetic tape is passed.

The apparatus can be made more sensitive in order to amplify the electrical signal, by 1) increasing the magnet's strength, 2) decreasing the size of the air gap, 3) increasing the current. The electrical signal or Hall voltage is proportional to the size of the current and to the strength of the magnetic field it senses. The magnitude of the field sensed is determined by the strength of the magnet as well as by the size of the air gaps. Since the air gap represents a "resistance" to the magnetic flux, a smaller air gap results in the Hall element sensing a larger magnetic field. The apparatus sensitivity to increased oxidation of the nickel is illustrated in FIG. 2 as determined with a one mil (0.0025 an) pure nickel foil. The electrical signal produced by the foil varies with the length, width, and thickness of the sample. The signal is directly proportional to sample thickness. Variation in the signal with sample length is shown in FIG. 3. FIG. 3 also shows the dimensional range of the sensed information, namely of about 21 mm. Thus, magnetic flux passed through the material is sensed up to 10.5 mm to either side of the center of the magnetic pole involved. If the material is further away than 10.5 mm, no signal is received since, as shown, the curve becomes flat beyond that distance. With a one mil (0.0025 an) nickel foil the accuracy of measurement reached is within two percent.

In order to monitor magnetically temperature, or partial pressure, the following criteria must be met. 1) A chemical agent must alter the magnetic property of the magnetic, or non-magnetic, material as a function of temperature or pressure in a unique, uniform, and reproducible manner. 2) The magnitude of the electrical signal must be related to the amount of material in the sample which has been altered in its magnetic properties. If length and width of a magnetic sample are kept constant, the signal is related only to sample thickness.

The apparatus of FIG. 1 has been used for the detection of oxygen with a tape of nickel as the active metal. Nickel metal, which is magnetic, reacts with oxygen to form nickel oxide, which is non-magnetic. The actual thickness of the oxide layer formed on the metal surface is determined by the partial pressure of oxygen, as well as by the duration and temperature of oxidation. The longer the time, the more elevated the temperature, the higher the oxygen partial pressure, the greater is the oxide thickness. When time and temperature are held constant, there is a one to one relationship between the oxide thickness and the oxygen partial pressure. If oxidations are carried out using nickel foil of a given thickness (say one mil, e.g., 0.0025 an), for a given partial pressure there will correspond not only a characteristic oxide thickness, but also a characteristic thickness of the nickel foil remaining unoxidized. During measurement the unoxidized portion of the sample causes an electrical signal; as the extent of oxidation increases, the thickness of nickel remaining unoxidized decreases, and so does the electrical signal. Conversely, the larger the oxygen partial pressure, the smaller the electrical signal.

The preceding satisfies the above-mentioned first criterion indicative of the effect of various oxygen partial pressures on nickel when time and temperature are maintained constant. If the above-mentioned second criterion is met, it will be possible to monitor the partial pressure of oxygen nickel oxidiation as a function of time. That this can be done is demonstrated by the following procedure.

Nickel oxidation data are gathered which relate oxide thickness to time with temperature and oxygen partial pressure maintained constant. These data permit predictions about the relative magnitudes of electrical signals obtained from oxidized nickel samples. If the second criterion is met, the following relationship should hold: When a strip of nickel foil produces a given electrical signal prior to oxidation, after oxidation it produces a smaller signal. The ratio of these signals should be identical to the ratio of the thickness of the unoxidized sample to the thickness of the nickel foil remaining after oxidation.

The preceding has been verified by the following experiment:

A furnace is used having a known temperature of 1000° C. A strip of nickel foil having a thickness of one mil (0.0025 an) was placed for one hour in the furnace containing an atmosphere of oxygen at a pressure of 0.1 atm. At the end of the exposure time the magnetic state which originally was 100 for pure nickel was sensed and found to be reduced to 80.2 (as stated in the first line of data of Table 4 herebelow).

TABLE 4

Predicted vs. Experimental Values for the Oxidation of Nickel in 0.1 atm of $O_2$ $$\frac{\text{Electrical signal produced by oxidized sample}}{\text{Electrical signal produced by unoxidized standard}} \times 100$$

| time (min) | Values predicted on basis of Gulbransen-Andrew data | Experimental Values | % Difference |
|---|---|---|---|
| 60 | 80.2 | 80.2 | 0 |
| 80 | 76.5 | 77.3 | 0.8 |
| 100 | 73.0 | 75.0 | 2.0 |
| 120 | 69.7 | 71.4 | 1.7 |
| 140 | 66.3 | 67.0 | 0.7 |
| 160 | 63.1 | 65.9 | 2.8 |
| 180 | 59.1 | 56.8 | 2.3 |

This means that 19.8% of the original one mil (0.0025 an) thickness of pure nickel had become an oxide layer. Since 1 mil = 254,000 A, the final thickness of oxide was:

19.8 × 254,000/100 = 50292 A.

Figure 4:
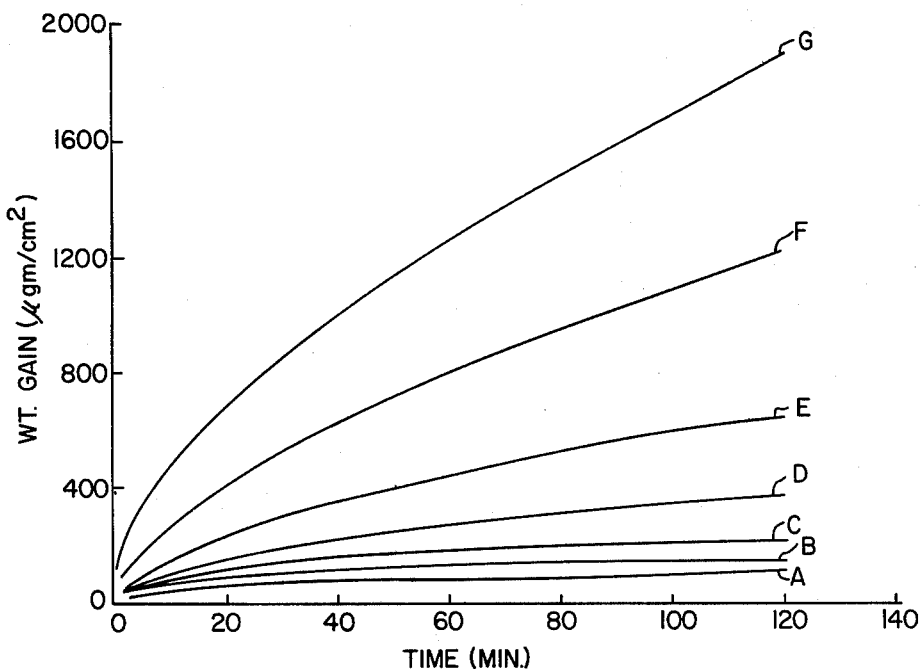
FIG. 4 shows a family of curves each corresponding to a definite temperature and indicating how much weight of nickel oxide is accumulated as a function of time for a given partial pressure of oxygen.

As shown by E. A. Gulbransen and K. F. Andrews in their article entitled "High Temperature Oxidation Of High Purity Nickel Between 750° and 1050°" and published in J. Electro-chem. Soc. 104,451 (1957), 62.9 A of oxide correspond to a weight gain of 1 μg/an2 for nickel oxide. Thus, 50292 A correspond to 800 Mg/an2. For each temperature, Gulbransen shows how to establish a graph of the nickel oxide accumulations as a function of time of exposure. FIG. 4 is a representation of such curves. Curves A through G correspond to temperatures of 750°, 800°, 850°, 900°, 1000° and 1050° C, respectively. Each curve has been traced for a partial pressure of oxygen of 7.6 cen. Hg. The amounts of oxide in μg/an2 are plotted along the ordinate axis, for time of exposure ranging between 0 and 120 minutes. Taking the abscissa of 60 minutes (the actual time of exposure in the experiment) and the ordinate 800 for the calculated accumulated weight, it appears that the operative point is exactly on the 1000° C curve. The experiment thus shows that by measuring the magnetic property of the nickel strip when reduced to 80.2% of pure nickel, an exact indication of the temperature is derived. With the same nickel strip of one mil (0.0025 an) thickness, a scale of electrical signal magnitudes from a maximum of 100 is established using the curves of FIG. 3, so that measurement of temperature becomes possible directly with the apparatus of FIG. 1.

Strips of pure nickel foil of one mil (0.0025 an) thickness were thus exposed to 0.1 atm of oxygen at 1000° C for varying periods of time. After each sample cooled, it was passed through the magnetic sensing apparatus, which recorded an electrical signal. The magnitude of every signal obtained with the apparatus of FIG. 1 was within 2 percent of that predicted on the basis of the thickness of the oxide layer formed, and in accordance with the curve of FIG. 2 and the data in the first line of Table 4.

It also appears from the above that the proposed magnetic measuring method is widely applicable. Modifications to the magnetic apparatus permit its operation over a large range of sensitivities. In addition, other magnetic and non-magnetic materials exist which can be altered as described earlier. The method makes it possible to measure temperature, or partial pressure, in many industrial processes.

Another typical application of the invention is the measurement of the temperature gradient existing within a furnace. To that effect, a three centimeter strip of nickel foil is placed in the center of the furnace so as to extend on either side of the central point and transversely of such hottest point therein. The strip is maintained under exposure to oxygen in the furnace at 0.1 atm partial pressure during a predetermined time. After exposure, the strip is taken out of the furnace and when it is back to ambient temperature, the apparatus of FIG. 1 is used to determine the present magnetic properties, e.g., the scaled temperature at the time of exposure. The values so derived are shown on FIG. 5. The oxide thickness at the center is the largest and corresponds to the hot point at 1000° C. Temperatures falls off on either side as shown along 970°, 950° down to 900° C.

Figure 5:
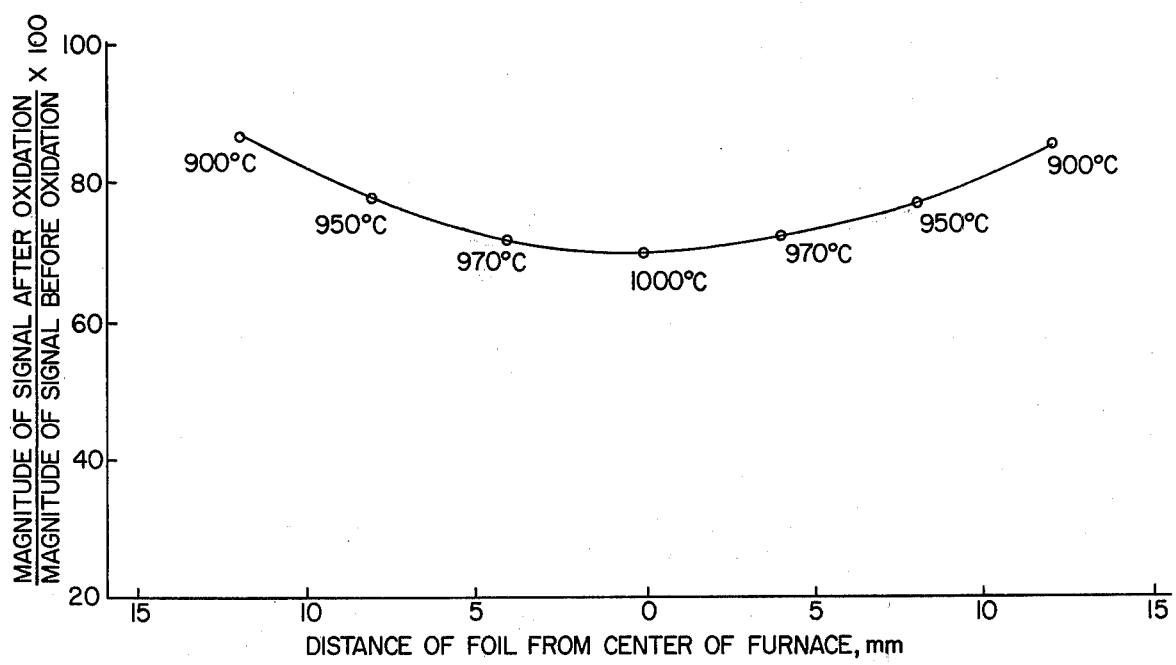
FIG. 5 shows gradients of temperature experienced by a strip of nickel in an oxygen furnace at different locations on the tape and as measured in accordance with the present invention.

The method, according to the present invention, for measuring temperature has several attractive features. It can be modified for use in other environments simply by choosing an appropriate magnetic (or non-magnetic) material and associated chemical reaction. As long as the two criteria earlier mentioned are satisfied, temperature measurement is feasible. The technique requires only simple equipment, for instance, the sensor apparatus shown in FIG. 1 and a strip of foil. Because of the compact nature of the magnetic foil "sensing" strip, temperature may be measured in completely closed areas, or in other places where conventional methods are inconvenient or inappropriate. The method can be made very accurate — possibly to an accuracy of ±1% — by a careful choice and preparation of the magnetic (or non-magnetic) material, the selection of the chemical reaction and the sensing device. As Table 3 shows, the calibrating measurements required initially can be made with unsophisticated equipment. FIG. 5 illustrates the range of measurement with the magnetic sensing apparatus shown in FIG. 1. The values obtained in practice prove to be within one to three percent of those predicted.

Temperature measurement is made by means of a change (for example, the oxidation of nickel foil) which is permanent. After the strip has been altered, for instance, oxidized, it can be transported, stored, etc. The interpretation of the oxidized strip (i.e., the determination of the temperature) need not be made under the same conditions as existed during the oxidation process, nor need the interpretation be made immediately after oxidation. This flexibility gives the measurement method a wide range of applications. In addition, the interpretation of the magnetic change is quick and easy. Once the strip has been magnetically altered, temperature can be determined directly by passing the strip through a device similar to the apparatus of FIG. 1.

If the temperature is fixed, rather than the partial pressure of the chemical agent reacting with the exposed magnetic tape, the same chemical reaction takes place as a function of time, but the altered magnetic properties of the strip provide instead, when measured by the apparatus of FIG. 1, an indication of the partial pressure.

We claim:

1. A method of measuring physical data relative to an industrial process involving a plurality of physical variables and a chemical agent, comprising the steps of exposing to said process at least one face of a probe in the form of a strip of known thickness and of material consisting of a composition including as chemical constituent a chemical element having an affinity for said chemical agent when exposed thereto under said physical variables, whereby said strip is permanently altered in a direction normal to said face by the chemical reaction between said chemical element and said chemical agent to an extent depending upon time of exposure and the conditions of said physical variables, said altered material having magnetic properties different from the unaltered material;

sensing the magnetic properties of said strip after exposure;

correlating the sensed magnetic properties with the alterations of said strip relative to said known thickness to derive a calibration of said magnetic properties in direct correlation with the time of exposure and the condition of said process physical variables in terms of a selected one of said process physical variables;

exposing to said process a second strip of material of identical dimension and composition to cause similar alterations under predetermined time of exposure and conditions of said process physical variables except said selected one;

sensing the magnetic properties of said second strip after said exposure; and reading physical data relative to the magnitude of said selected physical variable from said second sensing step by correlation with said earlier calibration;

with said selected one of said process physical variable being temperature, and with said reading of physical data being a temperature measurement.

2. The method of claim 1, with said chemical agent being oxygen, and with said material being pure nickel, whereby said nickel under exposure is at least in part altered to nickel oxide.

3. A method of measuring physical data relative to an industrial process involving a plurality of physical variables and a chemical agent, comprising the steps of exposing to said process at least one face of a probe in the form of a strip of known thickness and of material consisting of a composition including as chemical constituent a chemical element having an affinity for said chemical agent when exposed thereto under said physical variables, whereby said strip is permanently altered in a direction normal to said face by the chemical reaction between said chemical element and said chemical agent to an extent depending upon time of exposure and the conditions of said physical variables, said altered material having magnetic properties different from the unaltered material;

sensing the magnetic properties of said strip after exposure;

correlating the sensed magnetic properties with the alterations of said strip relative to said known thickness to derive a calibration of said magnetic properties in direct correlation with the time of exposure and the condition of said process physical variables in terms of a selected one of said process physical variables;

exposing to said process a second strip of material of identical dimension and composition to cause similar alterations under predetermined time of exposure and conditions of said process physical variables except said selected one;

sensing the magnetic properties of said second strip after said exposure; and reading physical data relative to the magnitude of said selected physical variable from said second sensing step by correlation with said earlier calibration;

with said selected one of said process physical variables being the pressure of said chemical agent, and with said reading of physical data being a pressure measurement.

4. The method of claim 3, with said chemical agent being oxygen, and with said material being pure nickel, whereby said nickel under exposure is at least in part altered to nickel oxide.

* * * * *